(12) United States Patent
Weyl et al.

(10) Patent No.: US 6,474,655 B1
(45) Date of Patent: Nov. 5, 2002

(54) SEAL FOR A SENSOR ELEMENT OF A GAS SENSOR AND METHOD FOR PRODUCING SAID SEAL

(75) Inventors: Helmut Weyl, Schwieberdingen; Bernhard Wild, Markgroeningen; Peter Dettling, Waiblingen, all of (DE)

(73) Assignee: Robert Bosch GmbH, Stuttgart (DE)

(*) Notice: Subject to any disclaimer, the term of this patent is extended or adjusted under 35 U.S.C. 154(b) by 0 days.

(21) Appl. No.: 09/600,512

(22) PCT Filed: Oct. 28, 1999

(86) PCT No.: PCT/DE99/03451
§ 371 (c)(1),
(2), (4) Date: Sep. 6, 2000

(87) PCT Pub. No.: WO00/29838
PCT Pub. Date: May 25, 2000

(30) Foreign Application Priority Data

Nov. 16, 1998 (DE) .......................... 198 52 674

(51) Int. Cl.⁷ .......................... F16J 15/10; G01N 27/26
(52) U.S. Cl. .......................... 277/650; 277/937; 277/654; 204/424
(58) Field of Search .............................. 277/650, 654, 277/937, 934; 204/424, 429

(56) References Cited

U.S. PATENT DOCUMENTS

| | | | |
|---|---|---|---|
| 3,468,752 A | * | 9/1969 | Yamamoto et al. |
| 4,620,437 A | * | 11/1986 | Takami et al. .................. 73/23 |
| 4,958,514 A | * | 9/1990 | Takami et al. ............. 73/25.03 |
| 5,228,975 A | * | 7/1993 | Yamada et al. ............. 204/424 |
| 5,616,825 A | * | 4/1997 | Achey et al. .............. 73/23.31 |

FOREIGN PATENT DOCUMENTS

| | | |
|---|---|---|
| DE | 41 26 378 | 4/1992 |
| DE | 44 36 580 | 4/1996 |
| DE | 195 32 090 | 3/1997 |
| EP | 0 704 698 | 4/1996 |
| EP | 706 046 | 4/1996 |

* cited by examiner

Primary Examiner—Anthony Knight
Assistant Examiner—Alison K. Pickard
(74) Attorney, Agent, or Firm—Kenyon & Kenyon

(57) ABSTRACT

A seal is proposed for a sensor element of a gas sensor, in particular for determining the oxygen content in exhaust gases of combustion engines. The seal has a sealing element, which is fixed in position in a longitudinal bore of a metallic housing. The sealing element contains a mixture of steatite and at least one low-melting-point glass. To manufacture the seal, a prefabricated sealing ring made of a mixture of steatite powder and powdered glass is used, which is pressed in the longitudinal bore, the sealing ring being subjected to a thermal treatment, in which the glass is melted.

11 Claims, 2 Drawing Sheets

SEAL FOR A SENSOR ELEMENT OF A GAS SENSOR AND METHOD FOR PRODUCING SAID SEAL

FIELD OF THE INVENTION

The present invention relates to a seal for a sensor element of a gas sensor and to a method for fabricating the seal.

BACKGROUND INFORMATION

A previously proposed seal is described in German Published Patent Application No. 41 26 378. This seal uses a sealing element of steatite, which is pressed between two vitrified ceramic molded parts. The seal separates a section of the sensor element on the sampled-gas side from a terminal-side section of the sensor element, the terminal-side section projecting into a reference gas chamber, into which a reference gas is admitted. To manufacture the seal, an initially compressed sealing ring having the strength needed for an automatic assembly, is initially introduced into the longitudinal bore and is subsequently pressed between the two ceramic molded parts. When the sealing ring is pressed, it is transformed into steatite powder, which is then applied radially against the sealing element and against the inner bore of the housing, in the process, sealing off the sensor element in the housing. The thus formed seal has considerable residual porosity, which cannot be significantly reduced even by substantial pressing forces. This means that the steatite seal is only resistant in a limited fashion to liquid and gaseous fuel, as well as to water and water vapor. The fuel vapors present in the exhaust gas diffuse into the seal and are partially absorbed by the material of the seal. In response to heating of the gas sensor, the hydrocarbons are driven rapidly out of the seal by the high water vapor pressure. The component arriving in the reference gas chamber reacts there with the oxygen, the result being a change in the composition of the reference gas, thereby negatively influencing the sensor signal.

An improved sealing action with respect to fuel vapors is provided by a sealing arrangement described in German Patent No. 195 32 090. In this sealing arrangement, an additional sealing element made of boron nitride is pressed between two steatite sealing elements. The storage capacity of the boron nitride is many times less than that of steatite. However, to ensure a proper sealing function for this sealing arrangement, a narrowest as possible gap is required between the premolded boron nitride sealing ring and the probe housing, as well as between the boron nitride sealing ring and the sensor element. This places stringent demands on the dimensional accuracy of the individual elements.

A further specific embodiment of a seal provides for fixing the sensor element in a ceramic retaining member using a glass seal European Published Patent Application No. 706 046. A drawback of this approach, however, is that the sensor element is fixed in a substantially rigid fashion in the solidified glass melt. Depending on the temperature conditions prevailing during heating and cooling, or under the stress of external thermal shock, strain conditions are produced in the glass melt which lead to cracks in the same and act with a high level of tensile stress on the sensor element.

The object of the present invention is to fix the sensor element in position in a manner that is substantially free of forces, making it impervious to gas and fuel, and, moreover, enabling it to be integrated cost-effectively into large-scale production.

SUMMARY OF THE INVENTION

The seal according to the present invention, has the advantage of being impervious to gas, as well as to liquids, in particular to fuel, and, additionally, of being substantially temperature-resistant. The method according to the present invention is beneficial in that the manufacturing of the seal can be integrated cost-effectively in the mass production of gas sensors.

The measures delineated in the dependent claims render possible advantageous further embodiments of the seal specified in the main claim. Suitable glasses having the required low melting point are those containing lead, zinc, bismuth, or alkaline-earth metals in the form of oxides, borates, phosphates, or silicates, or a mixture thereof. An especially temperature-resistant, as well as gas- and fuel-impermeable seal is attained when the proportion of the steatite material amounts to at least 70% by weight, for example, between 70 and 95% by weight. The glass may be used, for example, with a proportion of 5 to 30% by weight. Optimal results were attained with a mixture ratio of powdered glass of 10–20% by weight and of steatite powder of 80 to 90% by weight.

DETAILED DESCRIPTION

Figure 1:
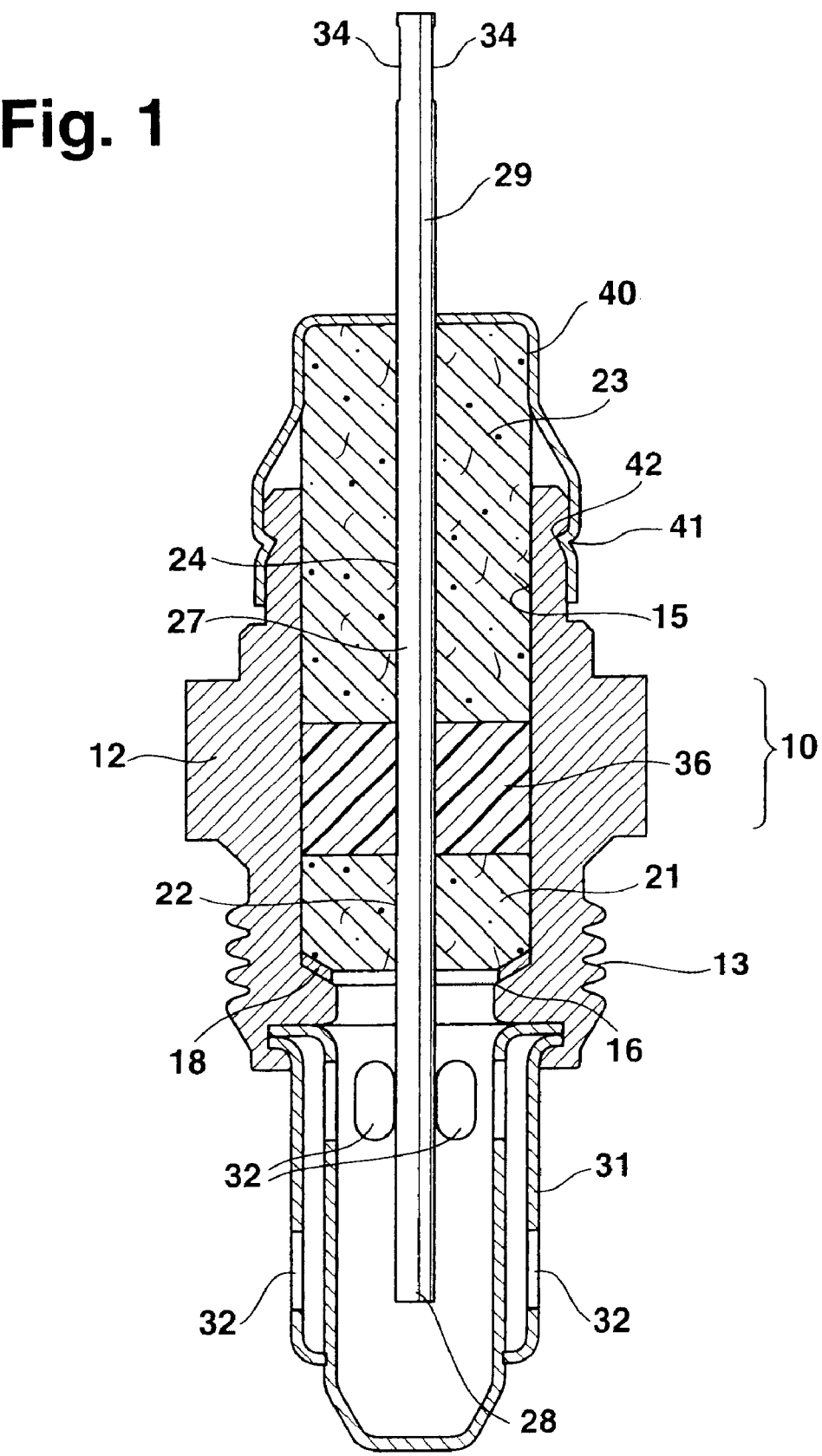
FIG. 1 illustrates a cross-section through a seal arrangement of a gas sensor.

FIG. 1 shows a part of a gas sensor, for example of an electrochemical oxygen sensor, including a seal arrangement 10, which is introduced into a metallic housing 12, and fixes in position a platelet sensor element 27. Housing 12 has a longitudinal bore 15, including a shoulder-shaped annular surface 16. Located on shoulder-shaped annular surface 16 is, for example, a metallic sealing ring 18, upon which a sampled-gas-side ceramic molded part 21 rests. Sampled-gas-side ceramic molded part 21 has a sampled-gas-side opening 22 which traverses straight through in the direction of longitudinal bore 15. In addition, housing 12 is provided with a winding 13 to be used as a fastening device for installation in an exhaust pipe (not shown).

In addition, a terminal-side ceramic molded part 23 is configured in longitudinal bore 15, set apart from the sampled-gas-side ceramic molded part 21. Terminal-side ceramic molded part 23 has a centrally disposed and traversing terminal-side opening 24, likewise running in the direction of longitudinal bore 15. Sampled-gas-side opening 22 of sampled-gas-side ceramic molded part 21, and terminal-side opening 24 of terminal-side ceramic molded part 23 run in alignment with one another.

Located in openings 22, 24 is sensor element 27, with its sampled-gas-side end section 28 and a terminal-side end section 29. Sampled-gas-side end section 28 projects out of housing 12 and is surrounded by a protective sleeve 31, which is secured to housing 12. Protective sleeve 31 has intake and exhaust ports 32 for the gas to be measured. At the terminal-side end section 29, the sensor element has connector contacts 34, which likewise project out of housing 12. Connector contacts 34 are contacted by a contact-type plug (not shown) provided with a connecting cable. Terminal-side end section 29 projecting out of housing 12 is surrounded by a protective sleeve (not shown), which protects end section 29 from environmental influences and, on the inside, forms a reference gas chamber.

Disposed between the sampled-gas-side ceramic molded part 21 and terminal-side ceramic molded part 23 is a seal 36, which is pressed between the two ceramic molded parts 21, 23. Even in the installed state, seal 36 is retained under a pressing pressure. The contact pressure required for this is applied by a metal sleeve 40, which presses on terminal-side ceramic molded part 23. In this context, metal sleeve 40 has, for example, a plurality of uniformly distributed claw-type fingers 41, which mate with notches 42 formed on housing 12. However, it is equally conceivable for metal sleeve 40 to be welded to housing 12.

Seal 36 is essentially made of steatite, with a proportion of 80–90% by weight, and of borosilicate glass, with a proportion of 10–20% by weight. To manufacture seal 36, an initially compressed sealing ring is used, which is fabricated from the mentioned mixture of steatite powder and fine powdered glass. The sealing ring is initially compressed in such a way that its plasticity, under the application of a pressing force, permits a deformation. After the sealing ring is inserted into longitudinal bore 15 on sampled-gas-side ceramic molded part 21, and the terminal-side ceramic molded part 22 is placed on the same, the pressing force required to press-work the sealing ring is applied by way of metal sleeve 40. After that, the subassembly, prefabricated in this manner, is subjected to a thermal treatment at approximately 600° C. Alternatively, a thermal treatment between 500° C. and 700° C. may also be performed. As a result of the thermal treatment, the powdered glass is melted in the steatite matrix and partially diffuses into its pores. This substantially reduces the permeability to gaseous and liquid hydrocarbons. It is also conceivable, however, to provide the thermal treatment during pressing of the sealing ring.

In a subsequent, further thermal treatment at approximately 600° C., the pressed sealing ring can be further compressed, resulting again in a further reduction in the existing residual porosity of the pressed sealing ring, thereby further improving the sealing action with respect to fuel. This thermal treatment, i.e., other heating operations, also take place in practical applications of the gas sensor, even when no pressing forces are applied in the process.

Figure 2:
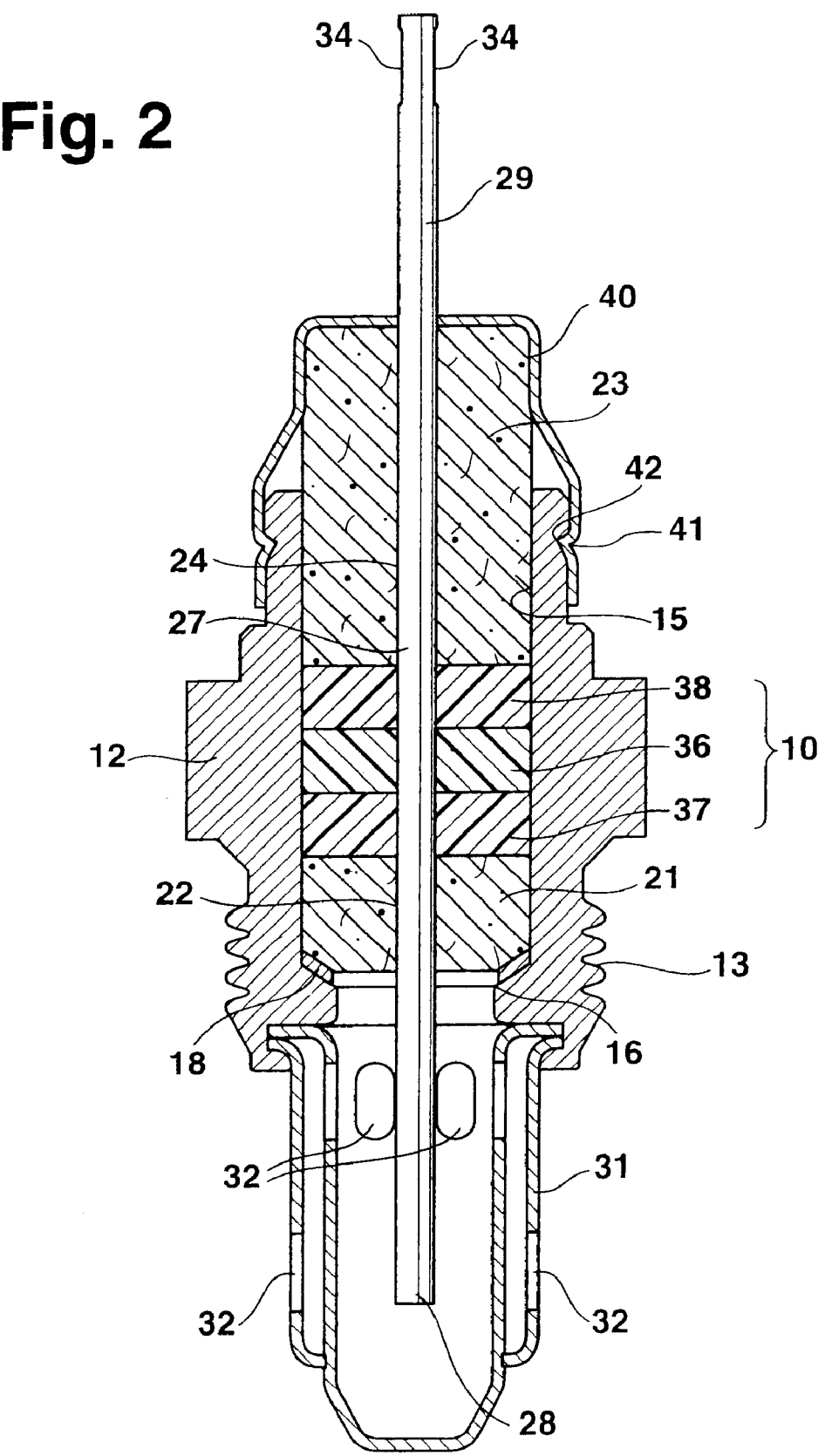
FIG. 2 another exemplary embodiment of a seal arrangement having a sandwich-type construction.

A further specific embodiment of a sealing arrangement 10 is evident in FIG. 2, equivalent elements being provided with the same reference numerals. In the case of the gas sensor of this exemplary embodiment, sealing arrangement 10 has a sandwich-type construction in accordance with the specific embodiment of the German Patent No. 195 32 090, seal 36 being arranged between a bottom sealing element 37 and a top sealing element 38. The composition of seal 36 conforms with that of the exemplary embodiment in FIG. 1. Sealing elements 37 and 38 are made, for example, of steatite. Sealing arrangement 10 is fabricated in the same manner as in the exemplary embodiment according to FIG. 1, sealing elements 37 and 38 likewise being used as initially compressed steatite sealing rings, which are pressed into longitudinal bore 15, together with the sealing ring of seal 36.

Besides sealing arrangement 10 in FIG. 2, other sandwich-type structures are also conceivable. An example is a sandwich-type arrangement of two sealing elements, the sealing element configured on the sampled gas side being made of steatite, and seal 36 being configured subjacent thereto on the terminal side.

The use of seal 36 in accordance with the present invention is not limited to sealing planar sensor elements in metallic housings. It is absolutely conceivable to use a seal of this kind or a sealing arrangement of this kind to seal so-called finger probes as well. In such an application case, the design of the prepressed sealing rings is adapted to the geometrical dimensions of the longitudinal bore and of the bearing surface of the housing and of the finger-shaped sensor element.

What is claimed is:

1. A seal in a sensor element of a gas sensor, comprising:
   a sealing arrangement for fixing the sensor element in a longitudinal bore of a metallic housing, wherein the sealing arrangement includes a sealing element containing a mixture of steatite and at least one low-melting-point glass;
   wherein the at least one low-melting-point glass includes one of lead, zinc, bismuth, and alkaline-earth metals in the form of one of oxides, borates, phosphates, and silicates.

2. The seal according to claim 1, wherein:
   the mixture includes the at least one low-melting-point glass according to a proportion of 5 to 30% by weight, and
   the mixture includes the steatite according to a proportion of 70 to 95% by weight.

3. The seal according to claim 1, wherein:
   the mixture includes the at least one low-melting-point glass according to a proportion of 10 to 20% by weight, and
   the mixture includes the steatite according to a proportion of 80 to 90% by weight.

4. The seal according to claim 1, wherein:
   the at least one low-melting-point glass includes a mixture of lead, zinc, bismuth, and alkaline-earth metals in the form of one of oxides, borates, phosphates, and silicates.

5. The seal according to claim 1, wherein:
   the seal is arranged in the longitudinal bore of the metallic housing between a sampled-gas-side ceramic molded part and a terminal-side ceramic molded part.

6. The seal according to claim 5, further comprising:
   a pressure element joined to the metallic housing and pressing on the terminal-side ceramic molded part.

7. A method for manufacturing a seal, comprising the steps of:
   plastically deforming under a pressing force in a longitudinal bore a prefabricated sealing ring made of a mixture of steatite powder and at least one low-melting-point powdered glass; and
   subjecting the prefabricated sealing ring to a thermal treatment in which the at least one low-melting point powdered glass is melted.

8. The method according to claim 7, further comprising the step of:
   performing the thermal treatment at one of during and following an application of the pressing force.

9. The method according to claim 8, wherein:
   a temperature of the thermal treatment is between 500 and 700° C.

10. The method according to claim 8, further comprising the step of:
    following the application of the pressing force, the seal is additionally subjected to the thermal treatment at between 500 and 700° C.

11. A seal in a sensor element of a gas sensor for determining an oxygen content in an exhaust gas of a combustion engine, comprising:
    a sealing arrangement that fixes the sensor element in a longitudinal bore of a metallic housing, wherein the sealing arrangement includes a sealing element containing a mixture of steatite and at least one low-melting-point glass;
    wherein the at least one low-melting point glass includes one of lead, zinc bismuth, and alkaline-earth metals in the form of one of oxides, borates, phosphates, and silicates.

* * * * *